(12) United States Patent
Richelsoph

(10) Patent No.: US 8,216,314 B2
(45) Date of Patent: Jul. 10, 2012

(54) DISTRACTABLE SPINAL IMPLANT ASSEMBLY

(76) Inventor: Marc Richelsoph, Charlotte, NC (US)

( * ) Notice: Subject to any disclaimer, the term of this patent is extended or adjusted under 35 U.S.C. 154(b) by 1184 days.

(21) Appl. No.: 12/030,226

(22) Filed: Feb. 13, 2008

(65) Prior Publication Data

US 2009/0204218 A1    Aug. 13, 2009

(51) Int. Cl.
*A61F 2/44* (2006.01)
(52) U.S. Cl. .................................. 623/17.15; 623/17.16
(58) Field of Classification Search ..... 623/17.11–17.16
See application file for complete search history.

(56) References Cited

U.S. PATENT DOCUMENTS

| | | | |
|---|---|---|---|
| 5,258,031 A | 11/1993 | Salib et al. | |
| 5,314,477 A | 5/1994 | Marnay | |
| 6,001,130 A | 12/1999 | Bryan et al. | |
| 6,443,987 B1 | 9/2002 | Bryan | |
| 7,217,291 B2 * | 5/2007 | Zucherman et al. | 623/17.15 |
| 7,850,733 B2 * | 12/2010 | Baynham et al. | 623/17.11 |
| 2004/0225363 A1 | 11/2004 | Richelsoph | |
| 2008/0140207 A1 * | 6/2008 | Olmos et al. | 623/17.16 |
| 2009/0088852 A1 * | 4/2009 | Chee | 623/17.16 |
| 2009/0093884 A1 * | 4/2009 | Bass | 623/17.16 |

* cited by examiner

*Primary Examiner* — David Bates
(74) *Attorney, Agent, or Firm* — Kohn & Associates, PLLC

(57) ABSTRACT

A spinal implant assembly includes a housing for containing a bearing member therein and seating within an intervertebral space and a bearing member disposed within the housing for enabling disc-like movement between vertebrae defining the intervertebral space. The combination of the housing and bearing member provide a distracting mechanism disposed within the housing halves 12, 14 for distracting the housing halves 12, 14 from a first condition in which the housing halves 12, 14 are floatable into the intervertebral space to a second condition in which the housing halves 12, 14 are distracted to fixedly engage the opposing vertebral services defining the intervertebral space. A method of inserting the spinal implant assembly into the intervertebral space includes the steps of inserting the spinal implant assembly into the intervertebral space and then distracting the spinal implant assembly from a first condition in which the spinal implant assembly is floatable into the intervertebral space to a second condition in which the assembly is distracted to fixedly engage opposing vertebral services defining the intervertebral space.

19 Claims, 18 Drawing Sheets

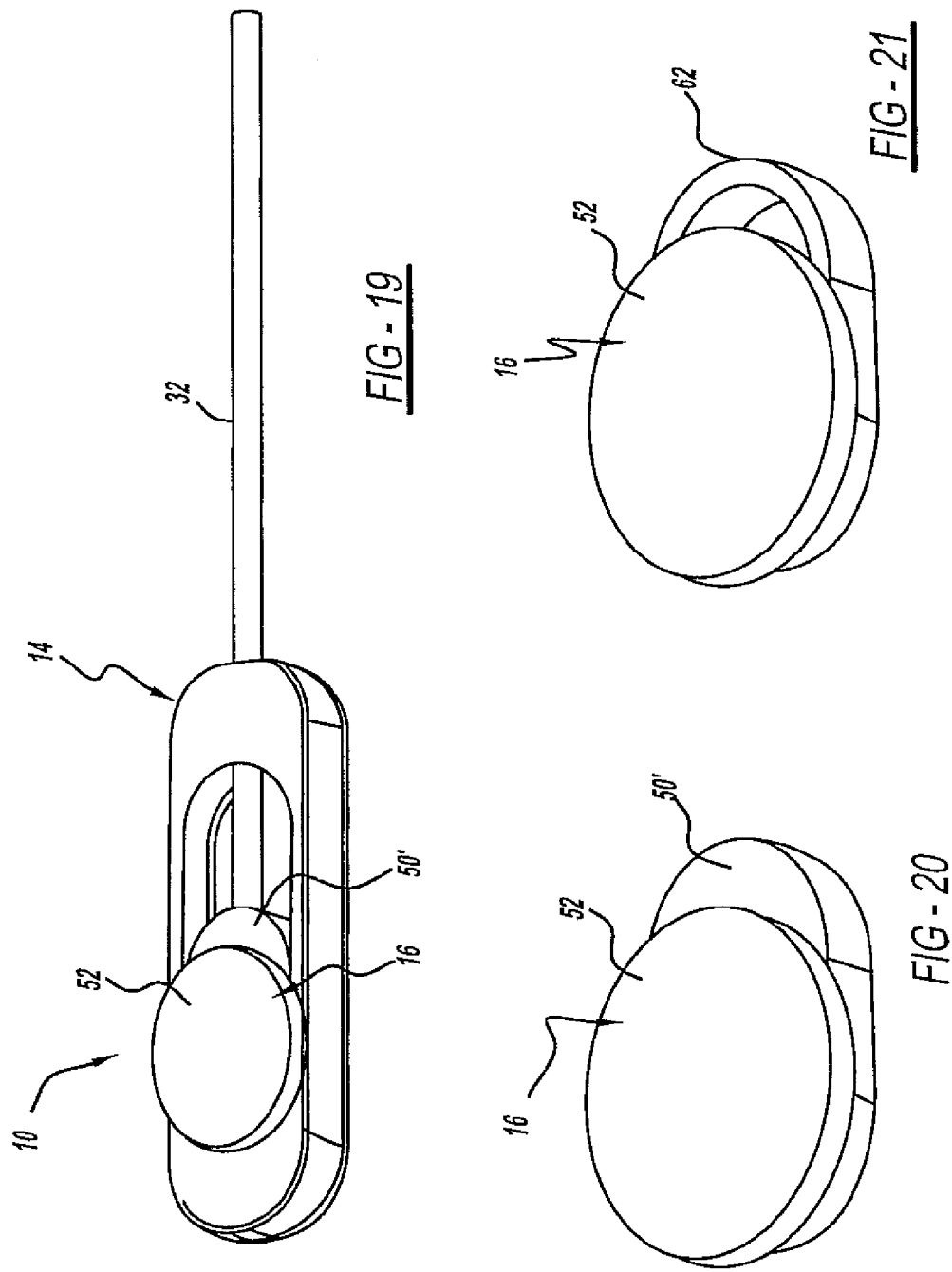

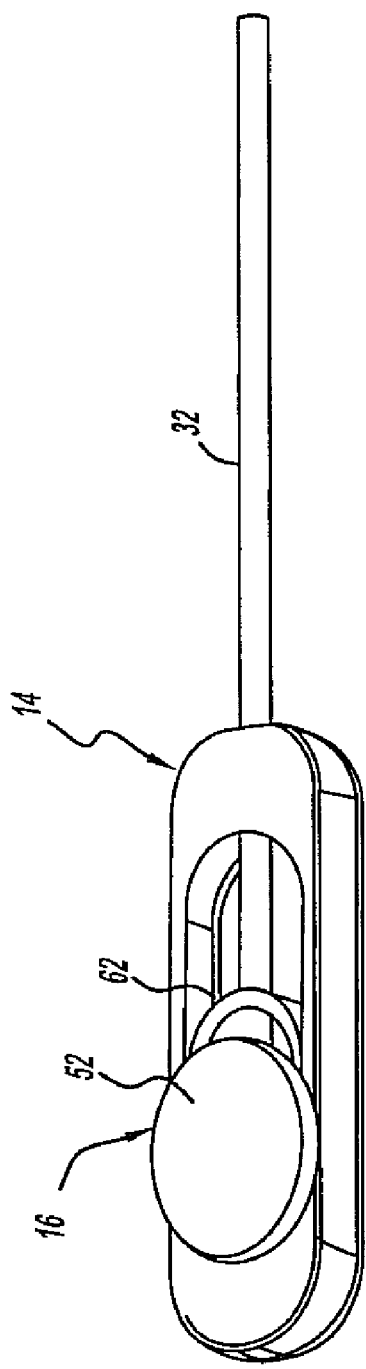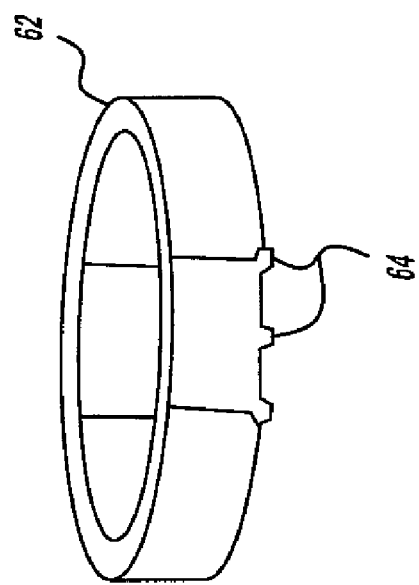

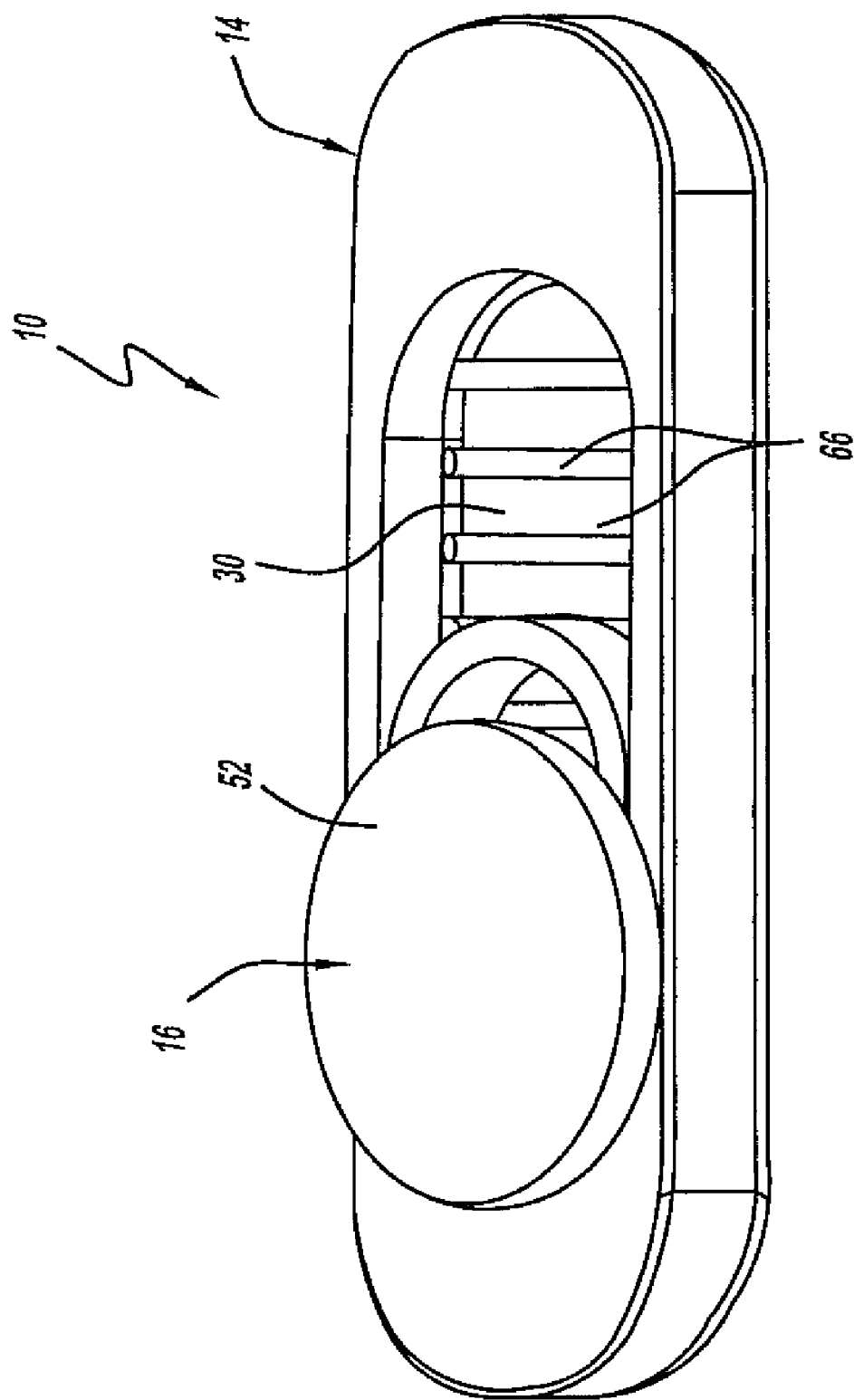

DISTRACTABLE SPINAL IMPLANT ASSEMBLY

BACKGROUND OF THE INVENTION

1. Technical Field

The present invention relates to a spinal implant assembly for implantation into the intervertebral space between adjacent vertebral bones to provide stabilization and continued post-operative flexibility, as well as restoring anatomical motion to the vertebrae defining the intervertebral space. More specifically, the present invention relates to an artificial intervertebral disc, sometimes referred to as an intervertebral spacer device, for functioning as a load sharing and bearing device for replacement of a damaged, decayed, or otherwise dysfunctional intervertebral disc.

2. Background Art

The spine consists of multiple flexible levels, each level consisting of a system of joints defined by adjacent vertebral bones. The system of joints includes vertebral discs, which are a two-part structure. The disc consists of a nucleus and an annulus. The system allows motion, while facet joints add proper stabilization to the spinal column. The disc allows motion and cushioning at each of the intervertebral joints.

The vertebral joint is subjected to varying loads and problems over time, including disc degeneration due to a variety of reasons. Disc degeneration can be attributed to aging, damage due to excessive loading, trauma, and other anatomical issues. Facet joints of the structure can be compromised due to the same reasons, as well as due to arthritic changes. Severe joint degeneration and failure often cause sufficient pain to require surgical intervention.

The conventional method of treatment for severe pain caused by spine joint problems is fusion at the damaged level of the spine. The treatment, if successful, fuses the damaged section into a single massive bone. The fusion of the joint eliminates motion of the joint, thereby reducing or eliminating pain at that level. Success rates for pain elimination are high for this method of treatment; however, since the entire spine works as a flexible load bearing system, fusion often results in other complications.

Fusing the spine at one or more levels alters the biomechanics of the spine at every other level above and below the fusion. If one level is fused, the loads are absorbed by one less disc into a system, which is not designed for such a change. Thus, the remaining discs must redistribute loads, each disc absorbing a greater load. In addition, the spine naturally flexes to absorb loads. A fusion alters the means by which the spine flexes. This also increases the loads on the remaining healthy discs. In turn, it is well understood that a complication of fusion is that additional fusions may be required in the future as other discs deteriorate due to the altered biomechanics of the spine. In other words, short-term pain relief is exchanged for long-term alterations to the spine, which, in turn, usually require further alterations by way of surgery.

There are numerous prior art patents addressing the issue of disc replacement. U.S. Pat. Nos. 6,443,987 B1 and 6,001,130, both to Bryan, disclose polymer composite structures for cushioning intervertebral loads. U.S. Pat. No. 5,258,031 to Salib, et al. and U.S. Pat. No. 5,314,477 to Marnay, disclose ball and socket-type implants addressing the issue of intervertebral mobility. These patents are exemplary of a first approach in the art using an elastomer as a motion and dampening structure and a second approach utilizing a ball and socket joint to create a moving pivot joint. There are many variations on these concepts, many include mechanical springs and are more complex structural mechanisms. A significant portion of the prior art addresses the issue of intervertebral motion, but do not address anatomical loading considerations, nor do the prior art address the possibility of multiple implants and the problems involved therewith. Problems such as stabilizing the intervertebral space are addressed, but other problems such as restoring anatomical motion to the vertebrae, especially where multiple implants are employed, are not addressed by the prior art.

The current state of the prior art artificial intervertebral discs are associated with various problems. For example, a number of implants constructed from polymers are of insufficient strength to work effectively in the higher loading areas, such as the lumbar area. Such polymers often take compressive sets so that the original height of the implant decreases over time. The surgeon must either compensate for the compression by initially using a larger polymer prosthesis and estimate compression, or use the approximately sized polymer prosthesis and later surgically replace the same once the irreversible compression of the prosthesis is unacceptable. This is commonly experienced where the implant is an attempt to mimic the disc structure and flexibility.

Implants constructed with ball and socket joints severely restrict or eliminate shock cushioning effectiveness of a normal disc. This type of implant can provide motion, but biomechanically, the ball and socket joint negatively affects other healthy discs of the spine. The result can be long-term problems at other levels of the spine, as seen with the current treatment of fusion.

Other implants, not discussed above, utilize bearing surfaces usually having polyethylene bearing against metal interfaces. Polyethylene is a bearing surface that is problematic in large joint replacement due to the wear properties of the material. Since artificial discs are intended to be implanted over long periods of time, such wear can be highly damaging to surrounding tissue and bone.

To insert an artificial disc assembly or like intervertebral implant, distraction of the otherwise collapsed intervertebral space is necessary. The intervertebral space is collapsed due to the deterioration of the natural disc, which has lost fluid therefrom, has lost structural integrity, or has a combination of both. Usually, an instrument is inserted into the intervertebral space and expanded, either by ratcheting, a screw mechanism, or the like to expand the intervertebral space wide enough to accept the spinal implant assembly. The intervertebral space is usually hyper-extended and then allowed to collapse about the implant. This hyperextension strains small muscles and otherwise strains the integrity of the joint structure.

In view of the above, it is desirable to provide a spinal implant assembly that stabilizes an intervertebral space and restores anatomical motion to the vertebrae defining intervertebral space. Further, it is desirable to provide the spinal implant assembly that does not require hyperdistraction of the intervertebral space in order to avoid trauma to the surrounding tissue.

SUMMARY OF THE INVENTION

According to the present invention, there is provided a spinal implant assembly including a housing for containing a bearing member therein and seating within an intervertebral space and a bearing disposed within the housing for enabling disc-like movement between vertebrae defining the intervertebral space. The assembly includes a distracting mechanism disposed within the housing for distracting the housing from a first condition in which the housing is floatable into the intervertebral space to a second condition in which the housing is distracted to fixedly engage the opposing vertebral surfaces defining the intervertebral space.

The present invention further provides a spinal implant assembly including a housing, a bearing disposed within the housing for enabling disc-like movement between vertebrae defining an intervertebral space, and an adjustment mechanism for adjusting a center of rotation of the assembly relative to the intervertebral space after the assembly has been inserted into the intervertebral space.

Additionally, the present invention provides a spinal implant assembly including a mechanism for stabilizing the intervertebral space and restoring anatomical motion to vertebrae defining the intervertebral space.

The present invention further provides a method of inserting a spinal implant assembly into an intervertebral space by inserting the spinal implant assembly into the intervertebral space and then distracting the spinal implant assembly from a first condition in which the spinal implant assembly is floatable into the intervertebral space to a second condition in which the assembly is distracted to fixedly engage opposing vertebral surfaces defining the intervertebral space.

The present invention further provides a method of inserting the spinal implant assembly into the intervertebral space by adjusting the center of rotation of the spinal implant assembly after the assembly has been inserted into the intervertebral space.

Additionally, the present invention provides a method of inserting a spinal implant assembly into an intervertebral space by inserting the spinal implant assembly into the intervertebral space, stabilizing the intervertebral space, and restoring anatomical motion to the vertebrae defining the intervertebral space.

Moreover, the present invention provides a method of inserting a spinal implant assembly into an intervertebral space by posteriorly inserting two spinal implant assemblies into the intervertebral space and adjusting the center of rotation of each of the implants in situ.

Additionally, the present invention provides an insert assembly for a spinal implant assembly including a cylindrical portion including a first end having a substantially flat surface and a bearing portion operatively connected to a second end of the cylindrical portion.

DESCRIPTION OF THE DRAWINGS

Other advantages of the present invention are readily appreciated as the same becomes better understood by reference to the following detailed description when considered in connection with the accompanying drawings wherein:

FIG. 19 is a top prospective view of the assembly shown in FIG. 18, wherein the bearing member includes a bearing surface;

FIG. 20 is an enlarged view of the bearing member shown in FIG. 19;

FIG. 21 is a prospective view of a further embodiment of the bearing member;

FIG. 22 is a prospective view of the bearing member shown in FIG. 21 disposed within a housing member made in accordance with the present invention;

FIG. 23 is a prospective view of a base member made in accordance with the present invention;

FIG. 24 is an assembly drawing of a bearing member disposed in the base member shown in FIG. 23, the base member 23 being disposed within the housing member made in accordance with the present invention;

DETAILED DESCRIPTION OF THE INVENTION

A spinal implant assembly made in accordance with the present invention is generally shown at 10 in the figures. Various embodiments of like structures will be indicated by like numbers.

The assembly 10 includes a housing consisting of housing halves, generally shown at 12 and 14. The housing 12, 14 combine to contain a bearing member, generally shown at 16, therein and the housing seats within an intervertebral space.

Figure 1:
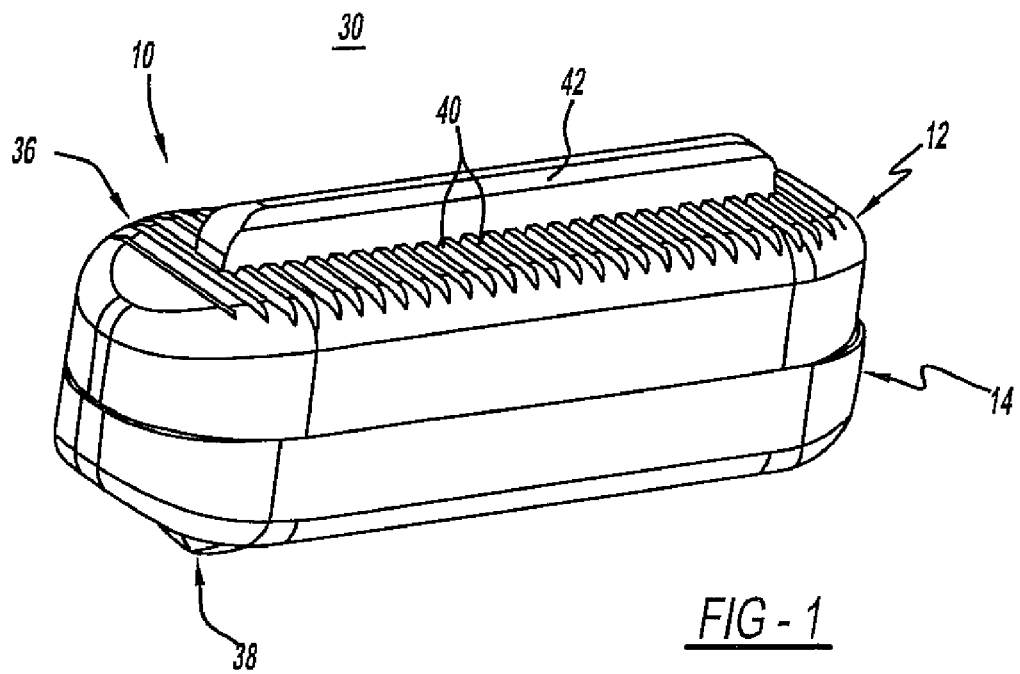
FIG. 1 is a prospective view of a spinal implant assembly made in accordance with the present invention.
Figure 2:
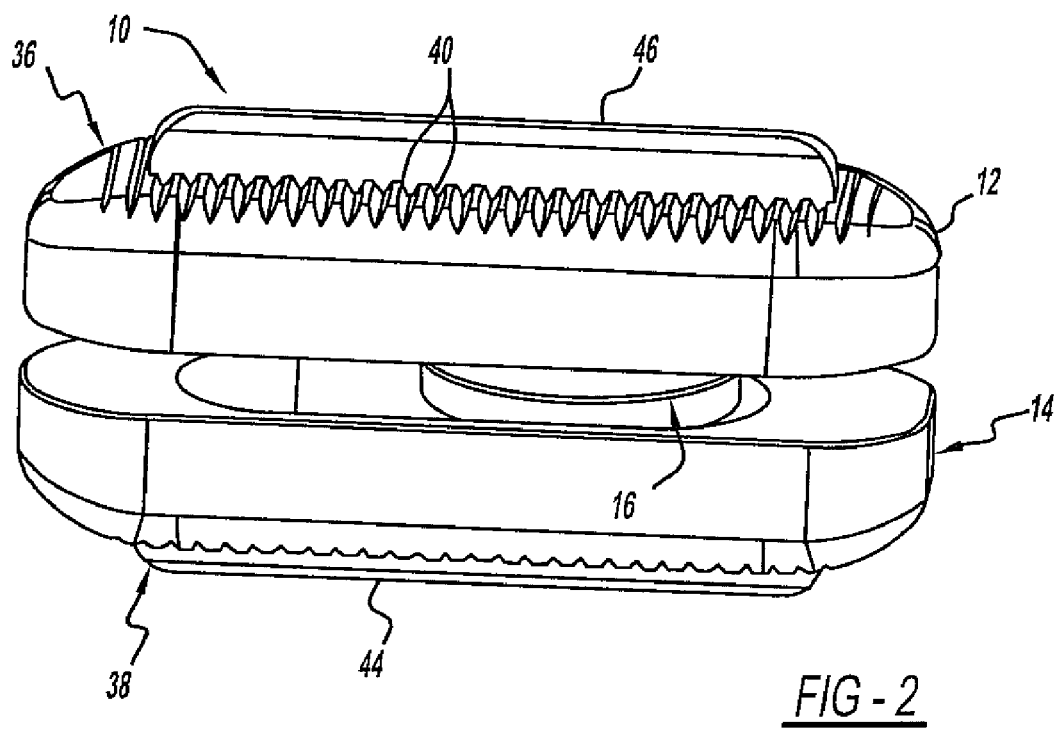
FIG. 2 is a prospective side view of the spinal implant assembly in a distracted condition.

As explained in more detail below, the housing halves 12 and 14 cooperate with the bearing member 16 as a distracting mechanism, whereby the housing halves 12 and 14 are distracted from a first condition, as shown in FIG. 1, wherein the housing is able to float into the intervertebral space as each of the housing halves contact each other and have minimum top to bottom height, to a second condition as shown in FIG. 2 in which the housing halves 12 and 14 are distracted to a maximal or a sub-maximal vertical height, separating the housing halves 12 and 14, to fixedly engage the opposing vertebral surfaces defining the intervertebral space. In this manner, the present invention provides a self-contained housing and bearing member, which can be inserted into a collapsed intervertebral space and then, the spinal implant assembly per se, distracts the intervertebral space to provide a bearing housing combination, which stabilizes the intervertebral space while restoring anatomical motion to the vertebrae defining the intervertebral space.

In order to accomplish this, and as set forth in more detail below, the spinal implant assembly 10 does not require a separate distracter instrument, which would otherwise hyperextend the intervertebral space to allow insertion of a prior art artificial disc or other spinal implant assembly. Rather, the present invention is capable of entering the collapsed intervertebral space without distraction and then is operated, as described in detail below, to actually distract the intervertebral space while becoming a functioning artificial disc assembly.

A significant further advantage is that access to the intervertebral space from the posterior aspect, is extremely limited due to the spinal cord and surrounding nerves. The smaller the assembly is, the better the insertion capability through the posterior aspect. Posterior insertion is favorable, as it requires less movement of internal organs and results in no scar tissue over major internal vessels that must be removed for reinsertion at a later date. Unlike other posterior concepts in the prior art, such as shown in US Publication 2004/0225363, to Richelsoph, and other artificial discs, the present invention provides a bearing member, which is self-contained within the fully collapsed first condition of the assembly 10 as discussed above. Other systems require that the disc be inserted at a full height and have fixed components, or that the bearing be inserted after the upper and lower sections are engaged with the vertebral end plates. An example of this is the Pro-Disc®, where an inlay is inserted afterwards. Insertion of other parts after the main components are implanted adds complexity to the procedure. Special instruments must be used for holding the implant upper and lower sections, while forcing distraction of intervertebral space of sufficient height to allow the bearing to be inserted. This complexity is a disadvantage. From the aspect of insertion from posterior, the use of bulky instruments is much more difficult. Distraction without the use of complex large instruments is highly beneficial, as obtained by the present invention, as described in greater detail below.

Figure 3:
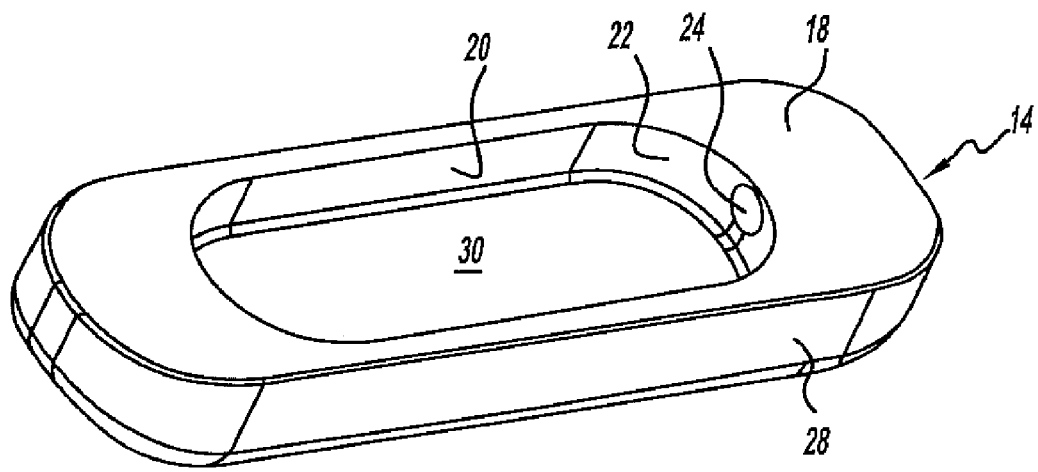
FIG. 3 is a top prospective view of a housing member of the present invention.
Figure 12:
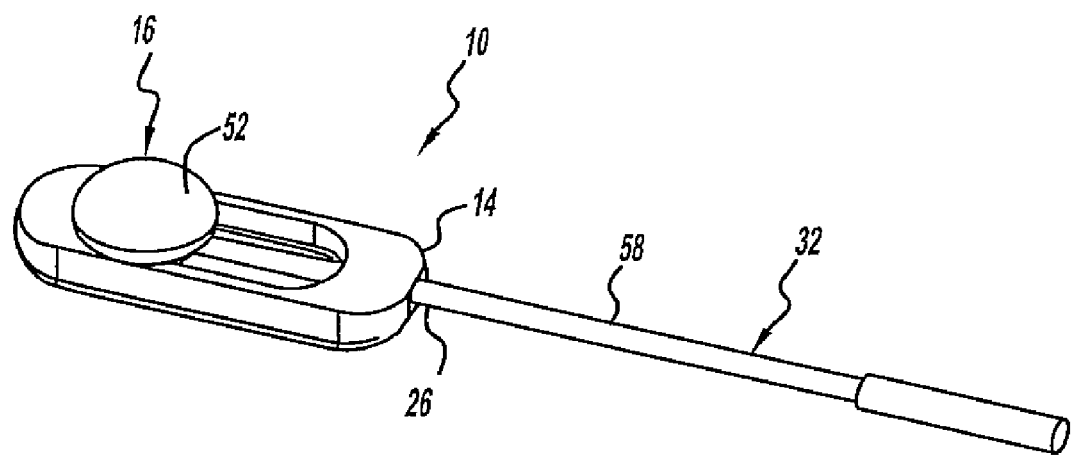
FIG. 12 is a prospective view of a bearing member in a housing member, the bearing member being operably connected to a device for moving the bearing member within the housing member.

An exemplary housing half is shown in FIG. 3. The housing half 12 includes a body portion 18 having a recessed cavity 20 therein. The cavity 20 includes a side wall 22 having an opening 24 extending from the side wall, through the body 18, exposed at 26 through the outer wall aspect 28, as shown best in FIG. 6. The cavity 20 includes a floor 30. The floor 30 in combination with the side wall 22 defines the slot or cavity 20 in each of the embodiments. In the embodiment shown in FIG. 3, the slot 20 provides a large amount of clearance vis-à-vis the contained bearing member 16 to allow the bearing member 16 to free-float the length of the slot 20 in addition to side to side, as the slot is wider than the base of the bearing member 16, as described in more detail below. The floor portion 30 acts as a ramp within the slot 20. That is, the floor portion changes in depth relative the side wall 22. In other words, at least one of the housing halves 12, 14 includes a floor portion 30 defining a ramping surface over which the bearing member seats and travels, whereby translating the bearing member from a first position where the ramp is at greatest depth and thereby the housing halves together are in the first condition as shown in FIG. 1 to a second position on the ramping floor surface 30, wherein the floor surface 30 is at a shallower depth, thereby distracting the housing halves 12, 14 and the surrounding intervertebral space to the second condition, as shown in FIG. 2. In other words, the bearing member 16 is first seated within adjacent cavities, wherein the floor portion 30 is at its greatest depth so that the housing cavities combine between the two housing halves 12, 14 to completely contain the bearing member 16 while being in engagement with each other, as shown in FIG. 1. As shown in FIG. 12, a device generally shown at 32 extends through the opening 24, 26 in the housing half 12 so as to be in engagement though an opening in the bearing member, as described below, so as to engage the bearing member 16. Hence, each of the housing members 12, 14 includes a recessed opening therein juxt opposed to each other defining the internal housing cavity when the housing halves 12, 14 are combined as in FIG. 1. The bearing member 16 is seated and contained therein. At least one of the housing halves 12, 14 includes the ramping surface 30.

Figure 4:
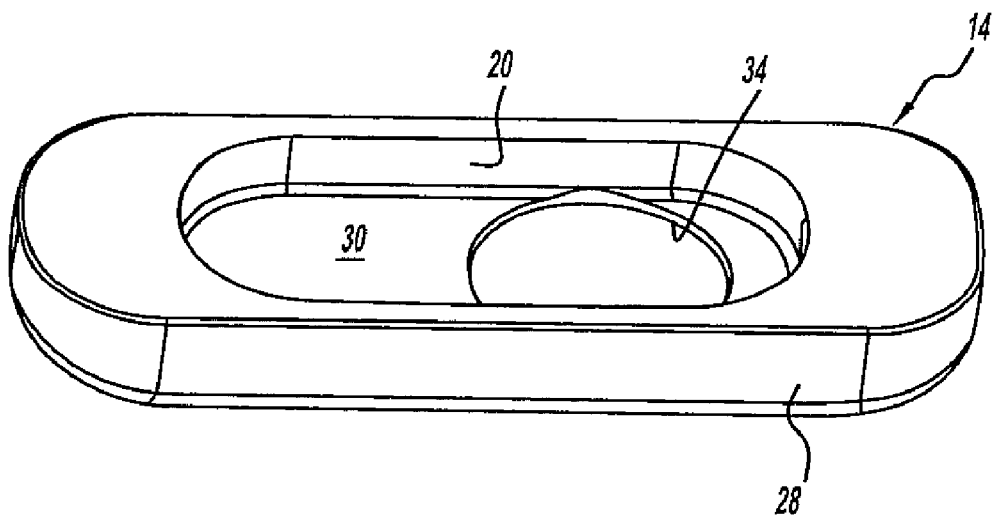
FIG. 4 is a top prospective view of a second half of a housing assembly made in accordance with the present invention.

As shown in FIG. 4, a bearing seating cavity 34 is machined into the ramping floor surface 30 of the housing half 12. The bearing seating cavity 34 is located at the desired location of the center of rotation of the implant once inserted. The ramping surface 30 rises within the cavity 20 to a sufficient height of desired distraction adjacent to the cavity 34 such that when the bearing 16 is pulled into position at the cavity 34, the base of the bearing slides into the cavity, thereby restricting motion of the bearing 16 to the clearance between the bearing member 16 and the cavity in all directions. Thus, the bearing seating cavity 34 is recessed relative to the high point of the ramping surface 30. The high point produces maximal distraction of the housing when the bearing member 16 is seated therein. The bearing member 16 is restricted from further translation on the ramping surface 30 when the bearing member 16 is seated in the bearing seating cavity 34. As stated above, the bearing seating cavity 34 seats the bearing member at a desired center of rotation.

Figure 5:
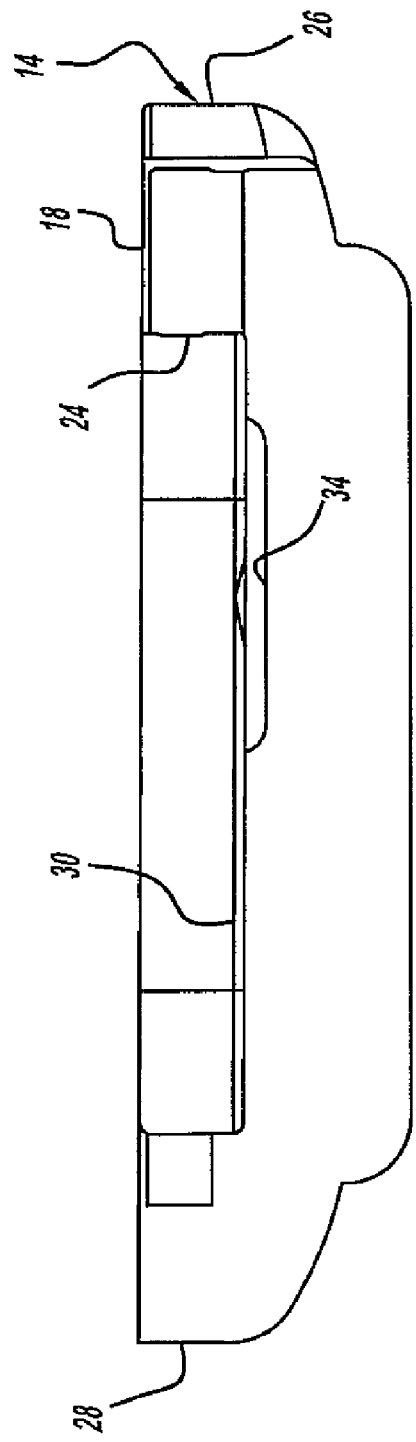
FIG. 5 is a side cross-sectional view of the housing member of FIG. 4.

FIG. 5 is a cross-sectional view showing the ramping surface 30 and cavity for seating the bearing member 34. The bearing member 34 must drop down into the cavity 34, therefore, the opening 24, 26 in the implant wall 18 must allow for clearance of the tool 32, which extends through the opening. That is, as the bearing travels up the ramp surface 30, the insertion member 32 must translate its angular relationship or otherwise adjust through the opening 24, 26, which is a tunnel through the wall 18. Likewise, when the bearing member 16 drops into the bearing seat cavity 34, a further translational adjustment need be made. Accordingly, the opening 24, 26 must be large enough or flared enough to allow for such change in angular relationship.

Figure 6:
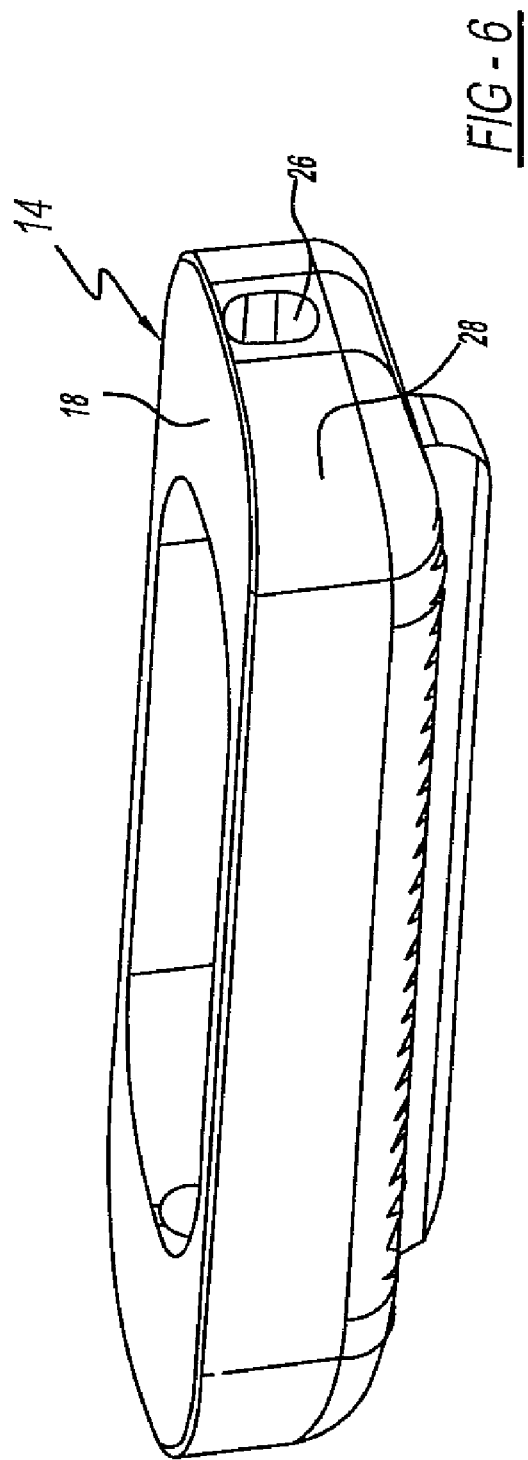
FIG. 6 is a substantially side prospective view of the housing member of FIG. 4.

FIG. 6 shows that the housing half 14 has an elongated opening 24, 26, to allow the instrument 32 to slide downwards as the bearing member 16 slides into the cavity seat 34.

The upper and lower outer surfaces generally shown at 36 and 38 in FIGS. 1 and 2 are structured so as to engage the adjacent vertebral surfaces defining the intervertebral space. The surfaces 36, 38 are shown to have multiple toothing 40 for engaging the vertebral surfaces preventing movement in one direction. In addition, fin-like projections 42, 44 prevent lateral movement. Other configurations well known in the art can also be used for preventing forward, backward, and lateral movements once the outside surfaces 36, 38 of the housing halves 12, 14 come into engagement with the vertebral surfaces defining in intervertebral spaces.

Figure 7:
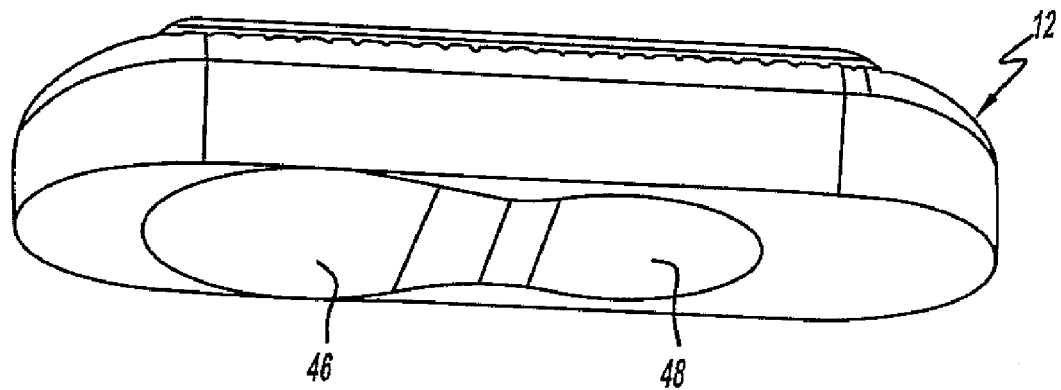
FIG. 7 is a prospective view of a second embodiment of a housing member of the present invention.
Figure 8:
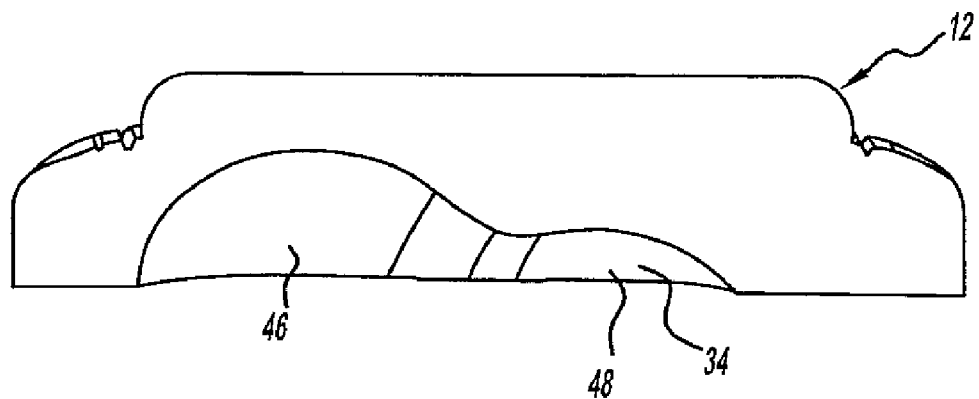
FIG. 8 is a cross-sectional side view of the housing member of FIG. 7.

FIGS. 7 and 8 demonstrate the basic concept behind the self-contained bearing of the present invention. The upper section 12 includes two distinct cavities of different dimensions. The first cavity 46 is large enough to allow the bearing member 16 to be completely held within, such that it is possible to allow the edges of the upper and lower housing halves 12, 14 to touch. In this position, the housing 10 is in the first condition shown in FIG. 1. The second cavity 48 is shallower, such that when the bearing member 16 is seated therein, the two housing halves 12, 14 of the implant assembly 10 are separated, as shown in FIG. 2, such that motion of the upper section 12 around the bearing member 16 is freely allowed. The cavity 46 that allows full collapse can be any shape, including cylindrical or spherical, or just a shelf that allows sufficient clearance for the implant sections 12, 14 to fully touch each other. There can always be partial collapse, such that small spacing exists between the two housing halves 12, 14, as touching is not a requirement, but touching creates the smallest possible implant structure, thereby allowing the freest insertion of the assembly 10 into the intervertebral space.

Figure 9:
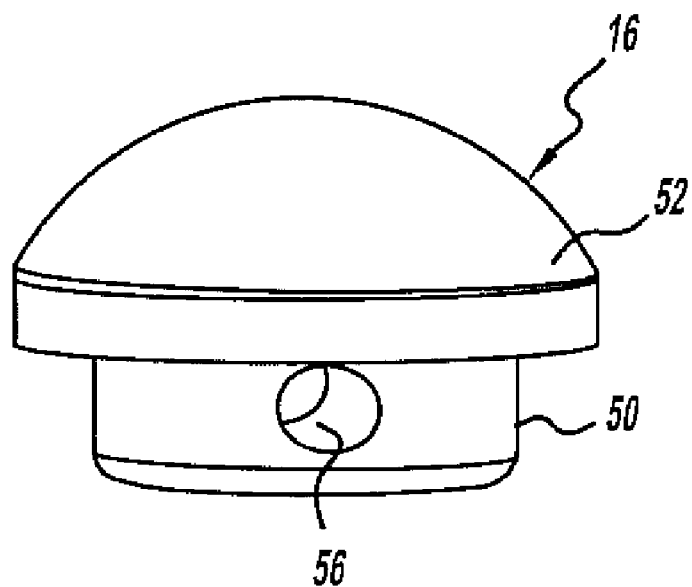
FIG. 9 is a side view of a bearing member made in accordance with the present invention.
Figure 10:
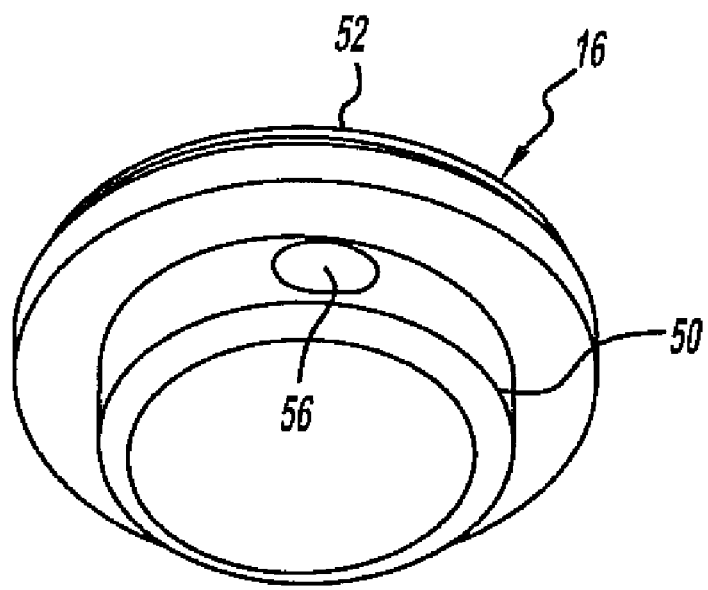
FIG. 10 is a bottom prospective view of the bearing member of FIG. 9.

FIGS. 9 and 10 illustrate the bearing member concepts. The bearing member 16 includes a cylindrical portion 50 for being seated within the seating cavity 34 and against the ramping surface 30. The bearing member 16 further includes a hemispherical portion 52 integrally connected to the cylindrical portion 50 providing a bearing surface against the bearing surface of the internal housing cavity, opposite to the ramping surface 30. The cylindrical portion 50 includes an opening or hole 56 therethrough for engagement and release by the instrument 32.

The hemispherical portion 52 is a highly polished surface, which can be treated with various surface treatments or coatings to improve wear characteristics. For example, the coatings can be selected from the group including diamond-like coatings, titanium nitrate, and many others known in the art that can be added to the surface of titaniums, cobalt chromes and stainless steels. Other polymers can be used as a bearing material, such as PEEK, as well as various ceramics known in the art. The bearing member 16 can be made from any of the materials that prove to have sufficient wear characteristics. Additionally, the cylindrical base portion 50 of the bearing member 16 can be various other shapes other than cylindrical. Several of these alternatives are discussed below.

Figure 11:
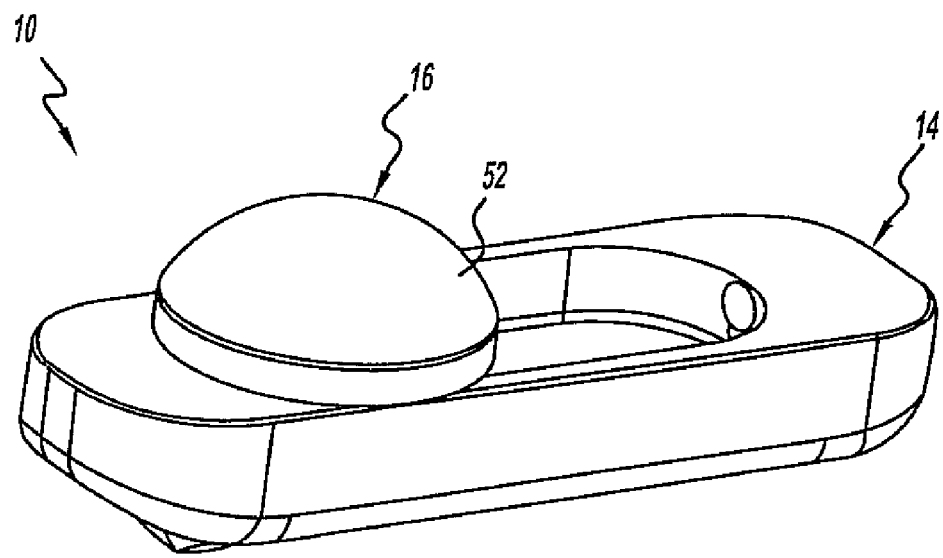
FIG. 11 is a prospective view of the bearing member disposed in a housing in accordance with the present invention.
Figure 13:
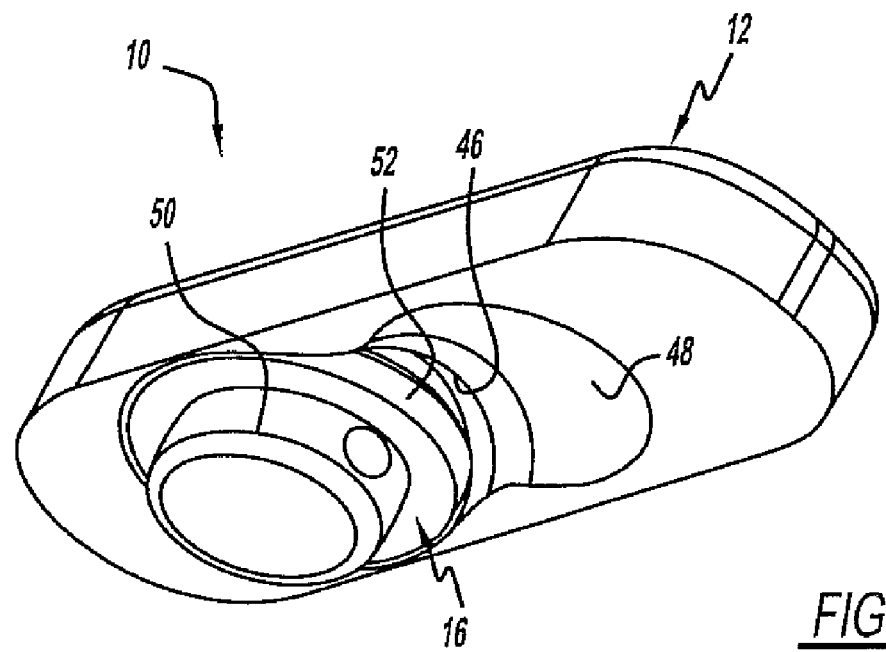
FIG. 13 is a prospective view of the bearing member including a bearing surface disposed in a housing half.
Figure 14:
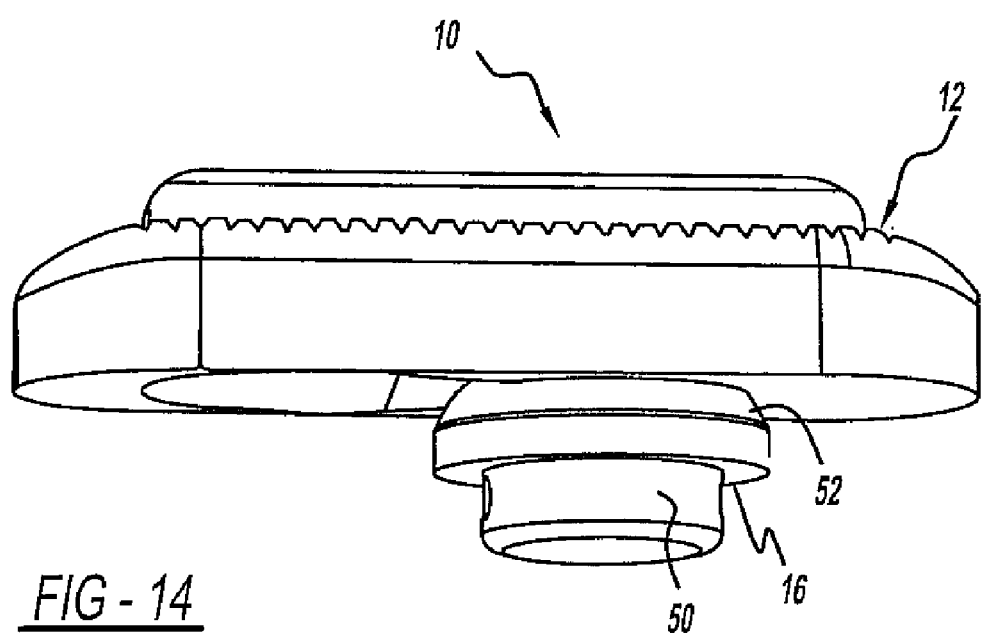
FIG. 14 is a substantially side prospective view showing the bearing member and housing of FIG. 13.

FIGS. 11 and 12 illustrate the translation of the bearing member 16 and its structure vis-à-vis the housing halves 12, 14. The bearing member 16 slides within the cavities in the housing halves 12, 14. Of course, the housing halves 12, 14 can be inverted so that the ramp slot is in the upper section and the dual cavities, as shown in FIGS. 13 and 14 seating the hemispherical portion 52 therein in the lower section. The instrument 32 includes a shaft 58, which temporarily attaches to the bearing member 16 through the opening 56. This allows for an attachment whereby the instrument 32 can pull the bearing member 16 into the proper location, thereby distracting the assembly 10. FIGS. 13 and 14 specifically show the hemispherical portion being moved from the deeper cavity 46, as shown in FIG. 13, to the shallower cavity 48, as shown in FIG. 14. More specifically, FIG. 13 shows the bearing member 16 fully seated within the deeper cavity 46, such that the height of the bearing member 16 does not contribute to the overall height of the assembly 10 while being self-contained within the implant assembly 10. FIG. 14 shows the bearing member moved into the shallower bearing surface in the upper section 12. The bearing member 16 slides from the deep cavity 46 into the much shallower bearing surface 48. Thus, as the bearing member 16 is moved, the upper and lower housing halves 12, 14 are forced apart. The amount of gap between the housing halves 12, 14 can be adjusted according to the design requirement and implant size in order to allow sufficient range of motion by the vertebrae surrounding the intervertebral space.

Figure 15:
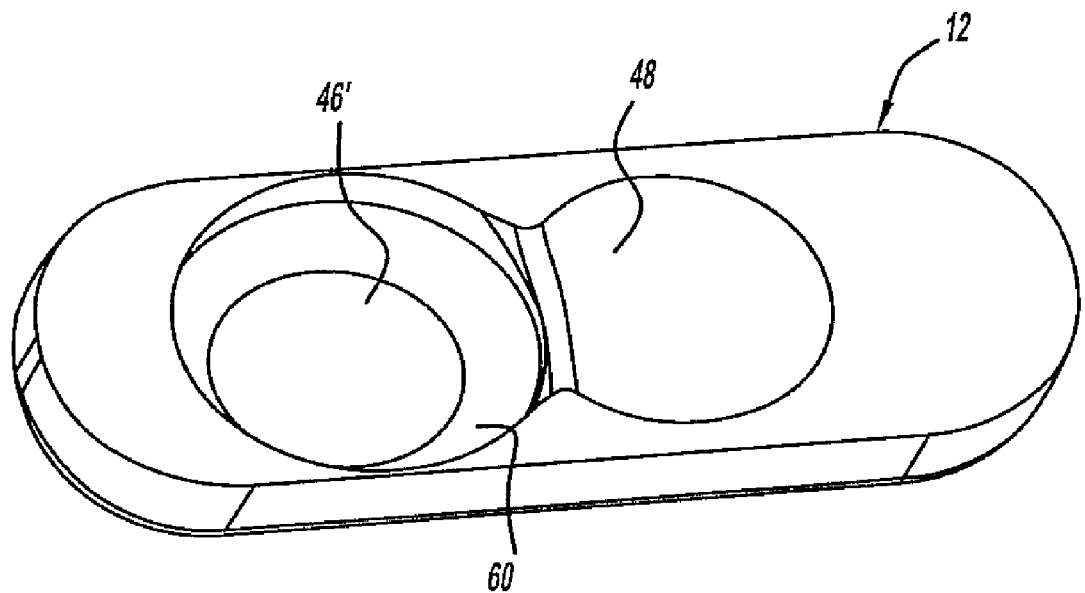
FIG. 15 is a top prospective view of a further embodiment of a housing member constructed in accordance with the present invention.
Figure 16:
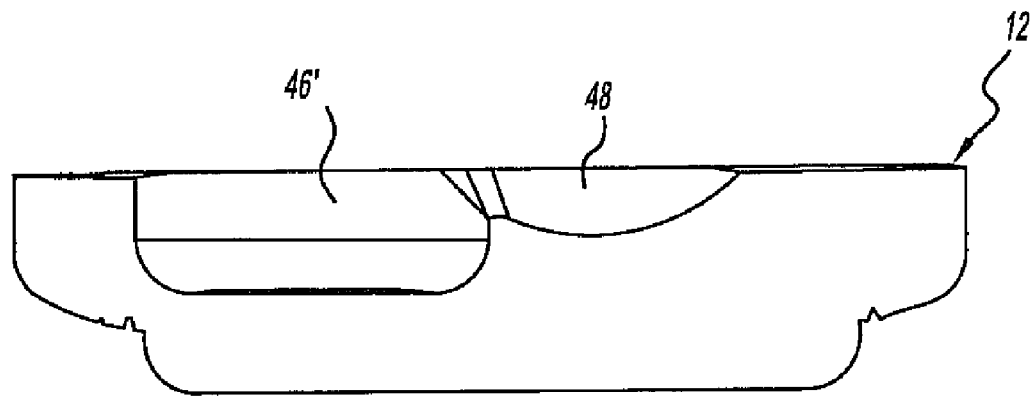
FIG. 16 is a cross-sectional side view of the housing member shown in FIG. 15.

FIGS. 15 and 16 show a variation in the size of the large cavity 46'. Instead of being spherical, the opening is cylindrical with blend radii 60 at the corners. The goal here is simply to create an opening large enough to allow the bearing member 16 to disappear inside of the housing halves, so shape can vary with no affect.

Figure 17:
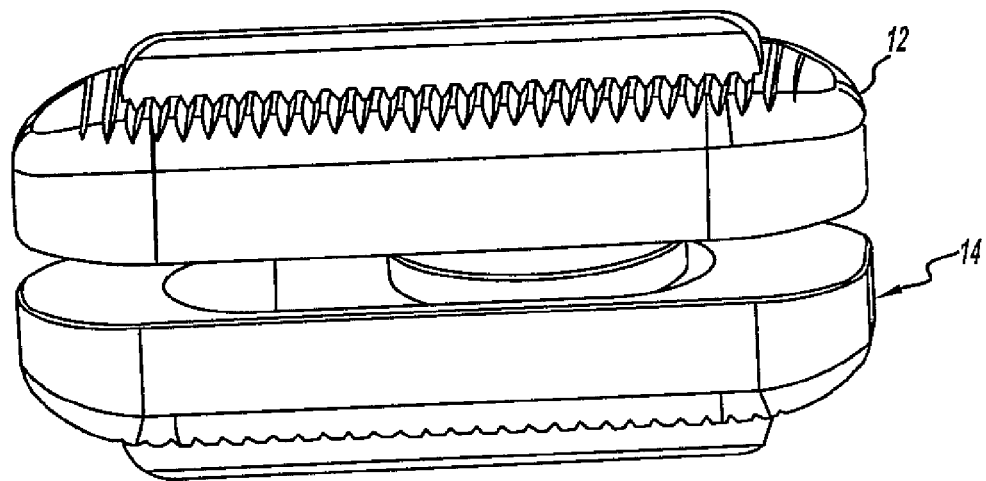
FIG. 17 is a shaded view of the assembly of the present invention.

FIG. 17 is a shaded structural image of the implant assembly 10 with the bearing member 16 in the bearing seat cavity 34 and in the shallow cavity 48, thereby spacing the housing halves best seen in shadow.

Figure 18:
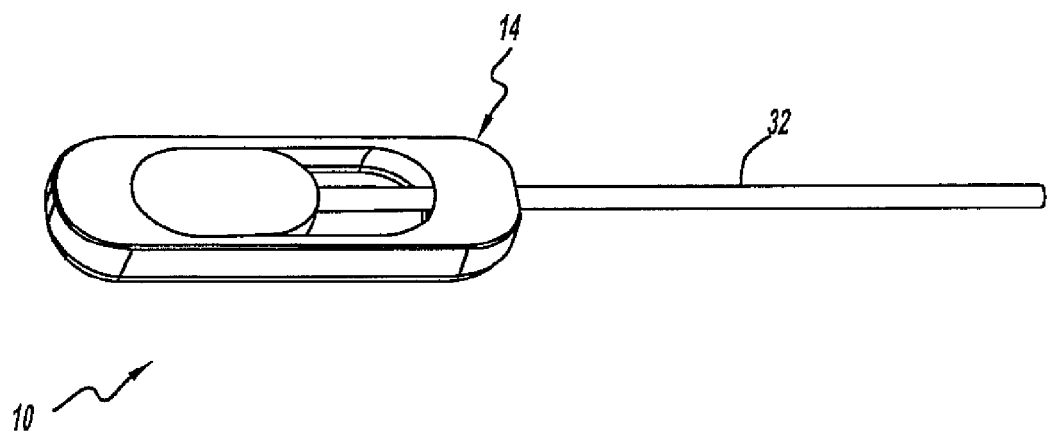
FIG. 18 is a substantially top prospective view of the present invention including an additional embodiment of the bearing member and housing.

FIG. 18 shows a variation in the housing and bearing design. Here, the bearing surface is machined directly into the base and therefore one piece with the base, as shown in detail in FIGS. 19 and 20. More specifically, the bearing member includes the hemispherical portion 52 and an oblong base portion 50'. In other words, instead of the base portion being cylindrical and smaller in circumference than the hemispherical portion 52, the base portion 50 is oblong. This shape, in combination with its seating in the cavity and the housing half 14, prevents rotation of the bearing member 16 relative to the housing member 14. This assures that the opening through the base portion 50' is always aligned with the opening 24, 26 through the housing 14. This allows for re-engagement of the instrument 32 with the bearing member 161 thereby allowing for re-engagement of the instrument 32 after implant, since rotation of the bearing member 16 resulting in misalignment of the opening therethrough is prevented. FIG. 21 shows a bearing member 16 and a separate base member 62. The base member 62 is disposed within the cavity of the housing member 14 for containing the bearing member 16 therein.

As best shown in FIG. 21, the entire bearing unit 16, 62 is capable of sliding within the opening in the housing member 16. The more gap between the bearing unit 16, 62 and the inside sides of the cavity within the housing 14, the more range of motion is allowed. FIG. 22 shows the separate bearing member 16 and base 62 combination, comprising the bearing member unit. This configuration allows for additional variations in the assembly, as first illustrated in FIG. 23. FIG. 23 shows that the base member 62 includes teeth 64 that extend downward for engaging grooves 66 in the floor 30 of the housing member 14. Of course, the base member 62 could include the recesses and the floor portion 30 include the teeth. In either event, the teeth 64 and groove 66 allow for locking of the position of the base member 62 relative to the lower section slot in the housing 14, wherever surgeon would desire it. Thus, the center of rotation of the implant can be adjusted wherever it must be, as opposed to utilizing a single recess for the bearing member 16. This adjustment can occur after the implant 10 is inserted in the intervertebral space and secured to the end plates. In the case where the bearing member 16 and base 62 are one piece, such as shown in FIGS. 19 and 20; the center of rotation can be moved to a fixed location. In the case where the base member 62 is a separate entity from the bearing member 16, as shown in FIGS. 23-24, a range of motion is established around the center of rotation as set by the surgeon. In other words, the bearing member 16 can move relative to the base member 62 while the base member 62 member can be selectively locked in position along a length of the housing members 12, 14. This approach provides unique advantages, including simplifying the alignment of two implants that would normally be critical. Secondly, the center of rotation can be established exactly where a surgeon wants it and then be adjusted if necessary. Although the teeth and grooves are shown in the lower section slot at the bottom or floor 30, and corresponding base surface, the features can be added to the sidewalls of the slot such as spring-like finger projections or teeth, not shown in the figures. The groove 66 shown in the floor portion 30 of the slot are shown in this manner for visibility in the drawing. The grooves do not have to go all the way across the slot and in fact, can be smaller indentations that do not interfere with the base of the bearing riding on the lower surface 30 of the slot.

Figure 25:
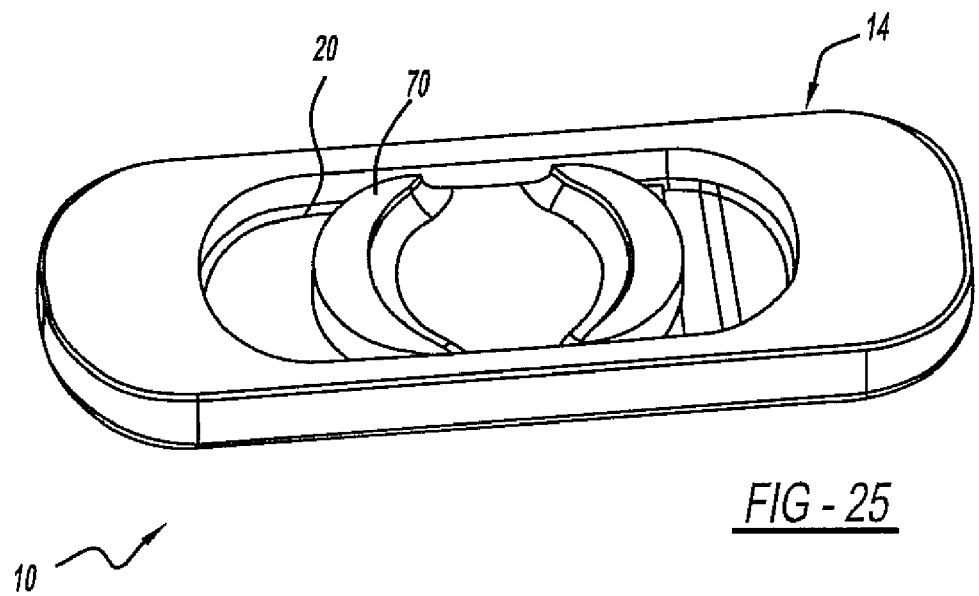
FIG. 25 is a prospective view of a further embodiment of the present invention.
Figure 26:
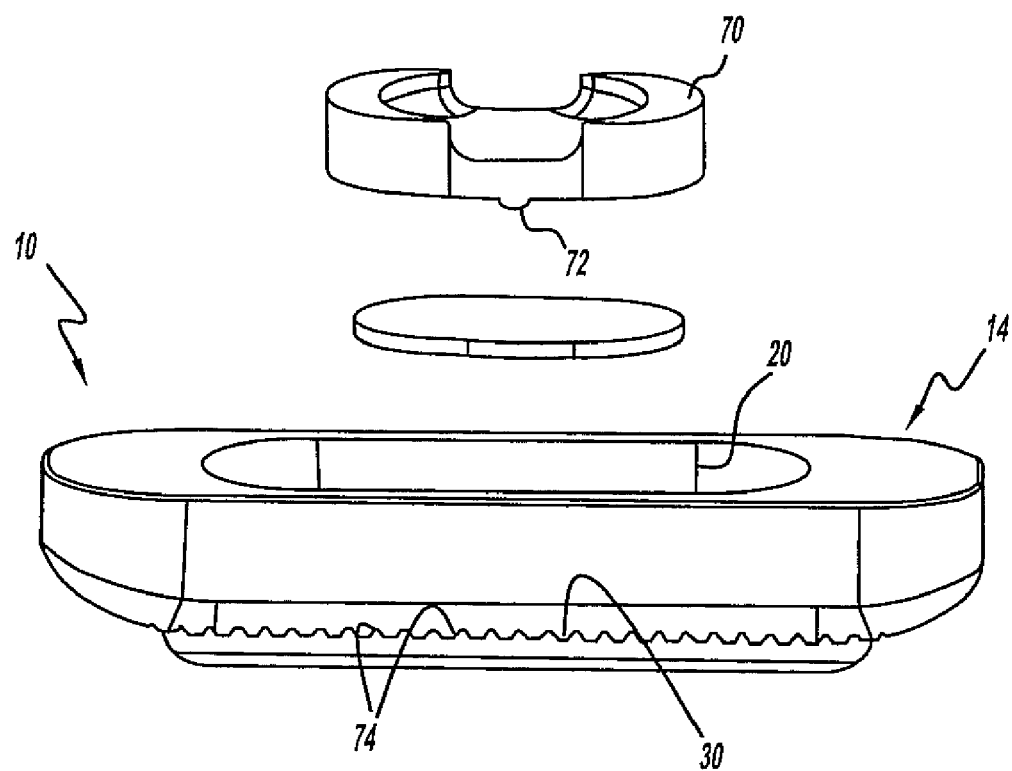
FIG. 26 is a substantially side prospective view, exploded, of the assembly shown in FIG. 25.
Figure 27:
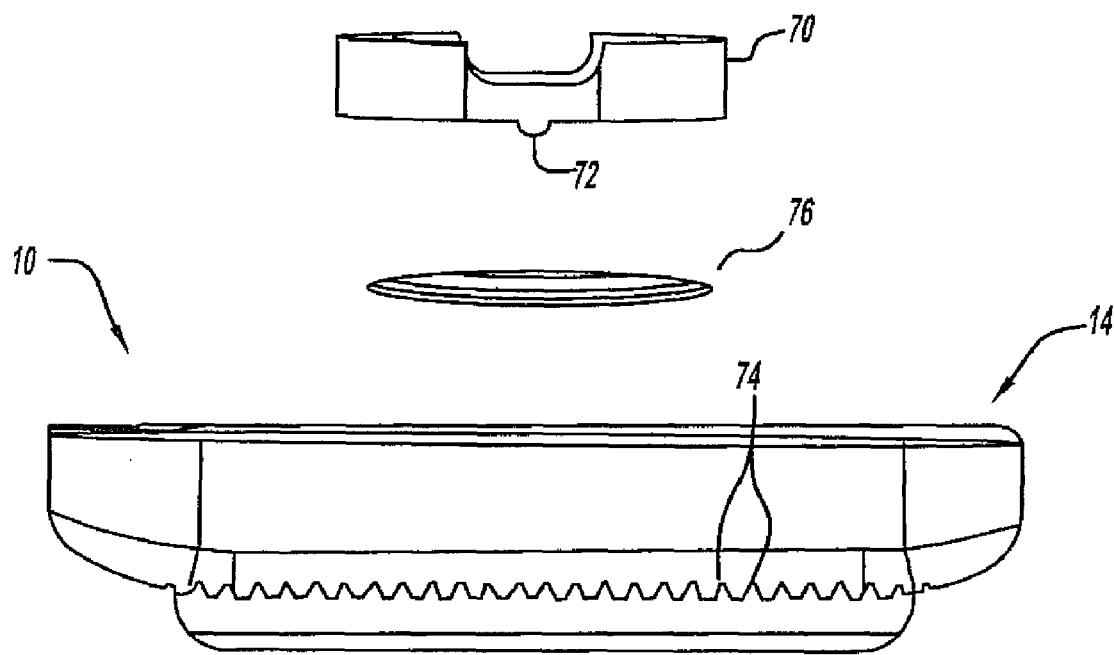
FIG. 27 is a side view of the assembly shown in FIG. 26, the housing member being shown in cross-sections.
Figure 28:
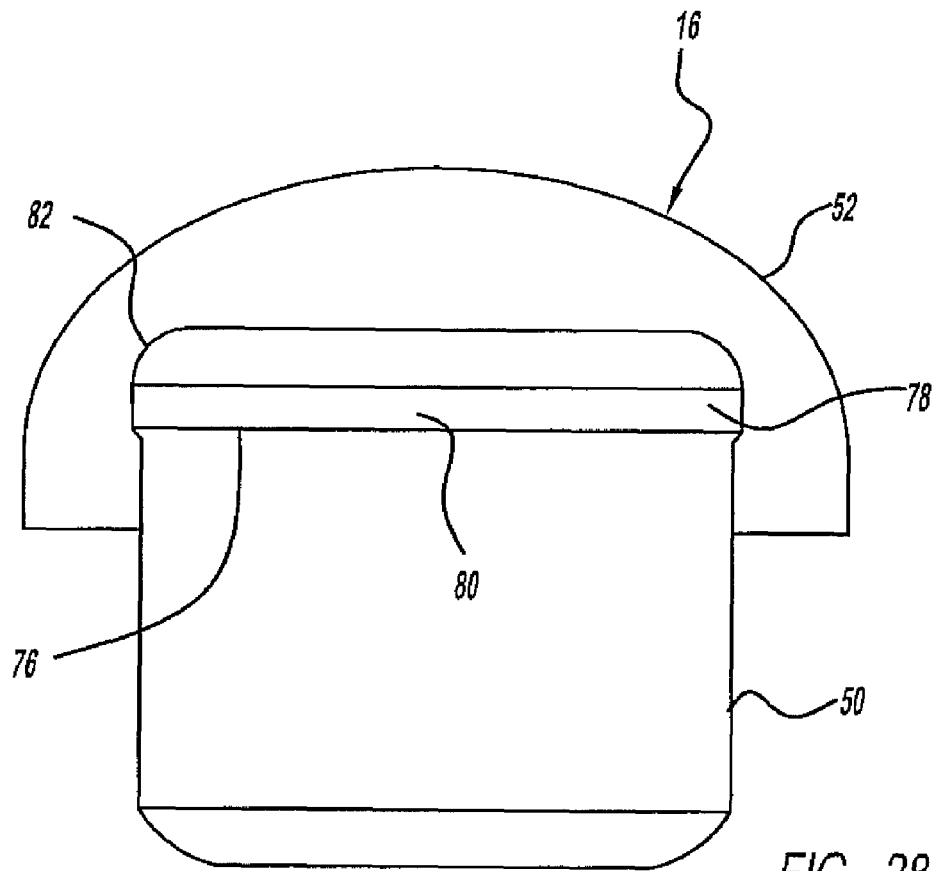
FIG. 28 is a cross-sectional side view of a further embodiment of the bearing member.
Figure 29:
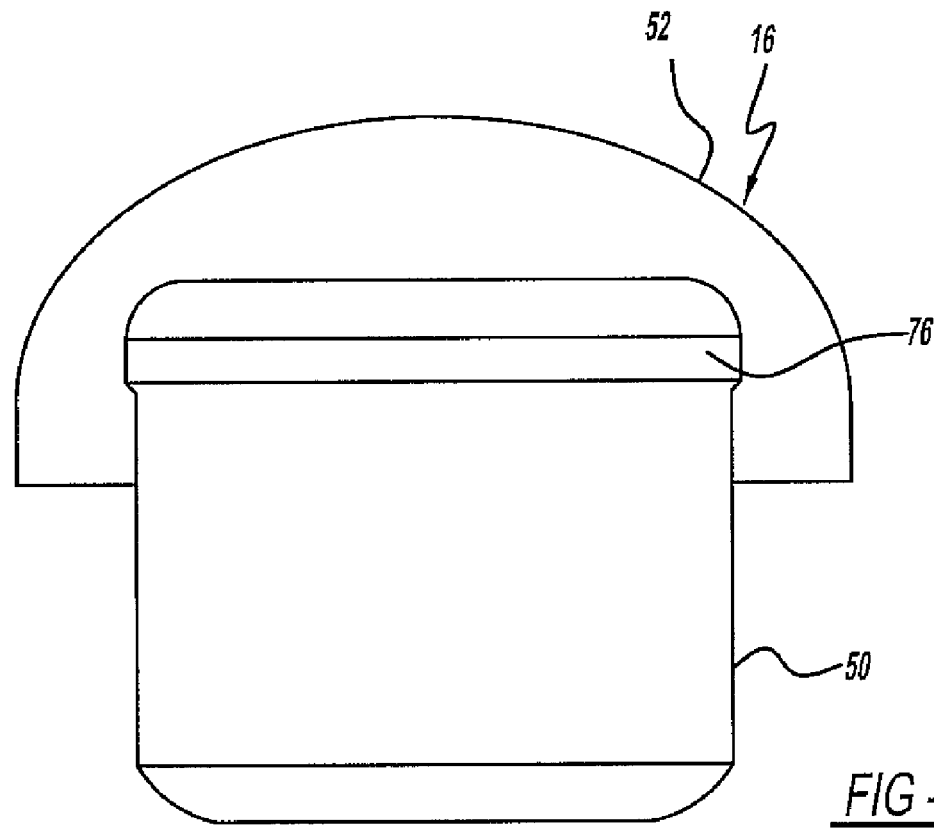
FIG. 29 is a shaded side view of the bearing member of FIG. 28.

FIG. 25 illustrates a different bearing and base unit 70, such that the base unit 70 slides within the slot 20 in the lower housing section 14 and is sized to abut against the sides of the slot 20. Motion of the bearing member 16 is carried within the base unit 70 itself. This base unit 70 is slid into the desired position and self locks into place between engagement of the tooth 72 and slot 74. This altered base unit design is extremely beneficial as illustrated in FIGS. 26-28. Placing two implants side by side in the spine some distance apart results in there not being a single point of rotation. In flexion-extension, there is no issue raised. However, the rotation of two independent implants utilizing the present invention compensate and work as a single implant. However, lateral bending is far more difficult. While removal of one level of lateral bending of the spine may not be critical, by allowing motion of the bearings in the cephalad/caudal direction, the bearing can move up or down to allow the implant to permit lateral bending. Accordingly, the present invention provides this full range of motion.

As illustrated in FIG. 26, a polymer insert 76 fits between the base portion 50 and the bottom of a slot that acts as a spring to allow up and down motion. The insert can be made from various materials having sufficient wear and flexibility properties.

FIG. 28 shows an alternative configuration, where the spring member 76 is sandwiched between a hemispherical head portion 52 and the stem cylindrical portion 50. Thus, the motion is contained in the bearing unit. The bearing hemispherical head 52 is separate from the stem base portion 50 such that the head 52 rests on the spring 76 or spring-like material that is sandwiched between the top of the stem or base portion 50 and the bottom of the hole 78 and the head portion 52. In this variation, the spring or retaining ring 76 snaps into a groove 80 in the base portion 50 and a second groove 82 in the head portion 52. At least one of the grooves 80, 82 must be elongated or of sufficient dimension to allow the head member 52 to slide up and down relative to the stem portion 50, thereby allowing anatomical motion of the adjacent vertebrae.

Figure 30:
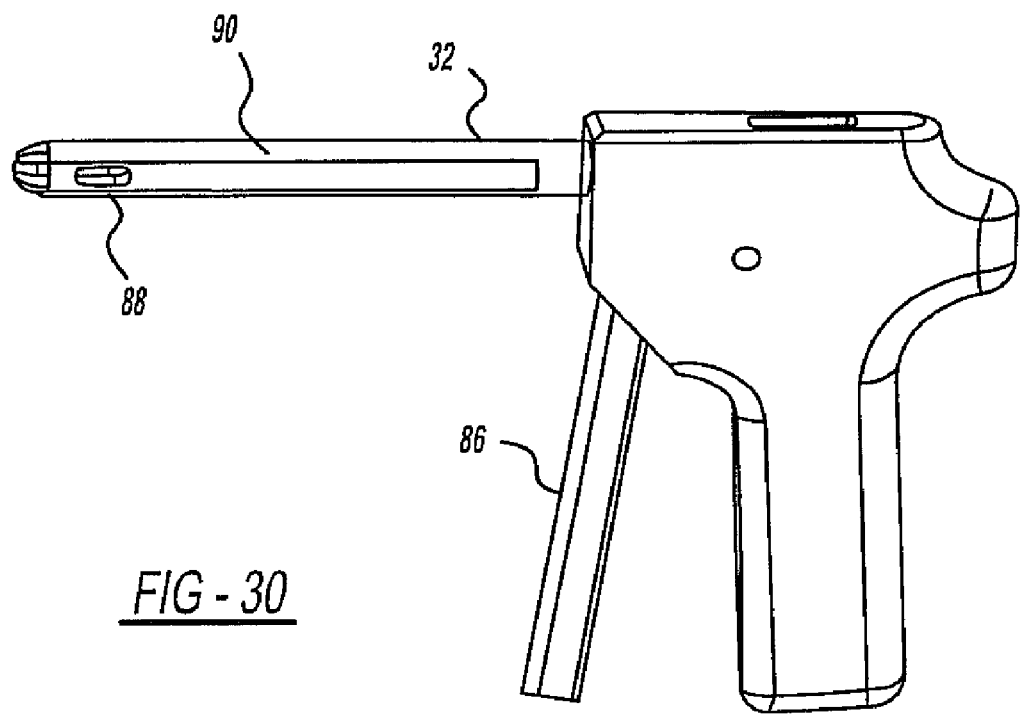
FIG. 30 is a side view of an instrument used in accordance with the present invention.

FIG. 30 shows the bearing member adjustment tool 32 including a trigger actuator 86 for adjusting pin members 88. In operation, the instrument 32 includes an elongated neck portion 90, which is inserted into the housing halves such that the pins 88 can engage or disengage the bearing member as desired.

The present invention includes variations to allow for insertion of multiple assemblies in accordance with the present invention. In certain circumstances, multiple assembly inserts require variations in adjustments to the assembly, as well as variations in the assemblies themselves so as to achieve anatomical motion restoration. For example, in certain circumstances, one assembly may be inserted with the hemispherical portion of the bearing member facing upward relative to the spinal column, a second assembly may be inserted with the bearing member having a hemispherical portion facing downward relative to the spinal column. By way of example, the housing member 12 in FIG. 10 is an upper housing having a flat ramp portion 92 leading to a cavity 94 therein for retaining the stem or base portion 50 of a bearing member and a relatively upside down configuration relative to a second assembly constructed in accordance with the present invention as described above and shown in FIGS. 1 and 2. Alternatively, there may be situations where a single assembly is inserted into an intervertebral space constructed in accordance with the embodiment shown in FIG. 1.

Figure 31:
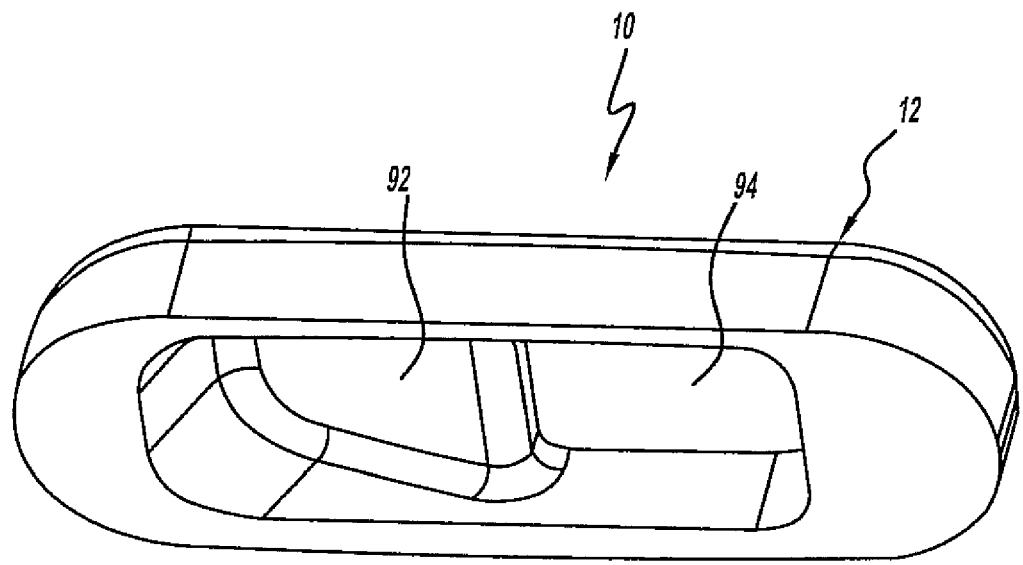
FIG. 31 is a prospective view of a further embodiment of the present invention.
Figure 32:
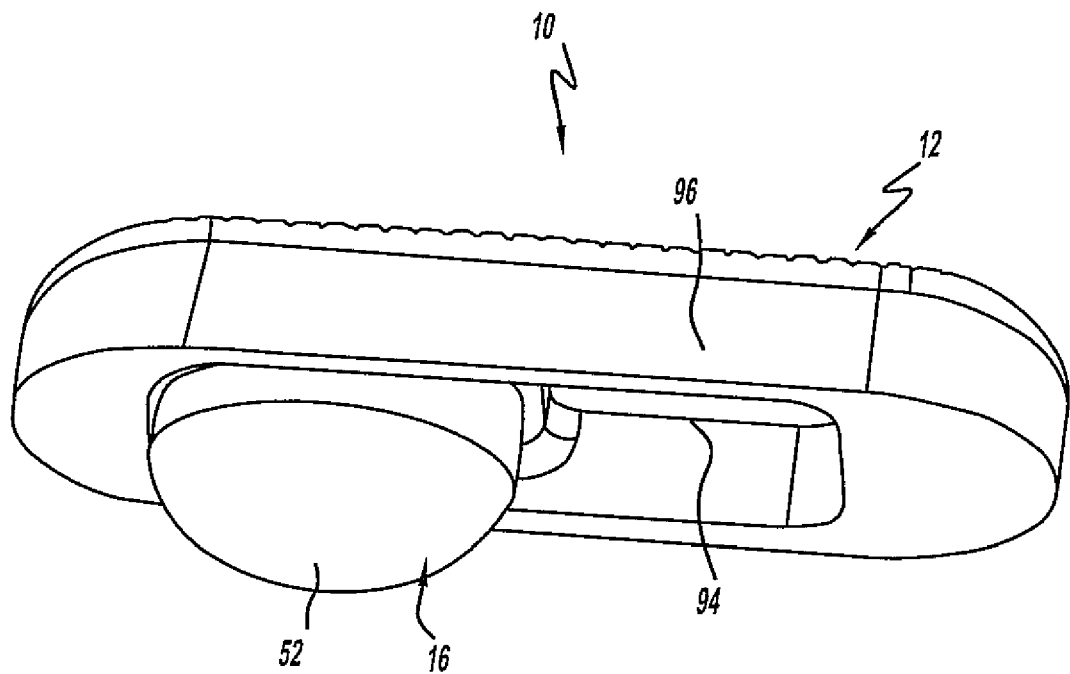
FIG. 32 shows the housing done in FIG. 31 with a bearing member disposed therein.
Figure 33:
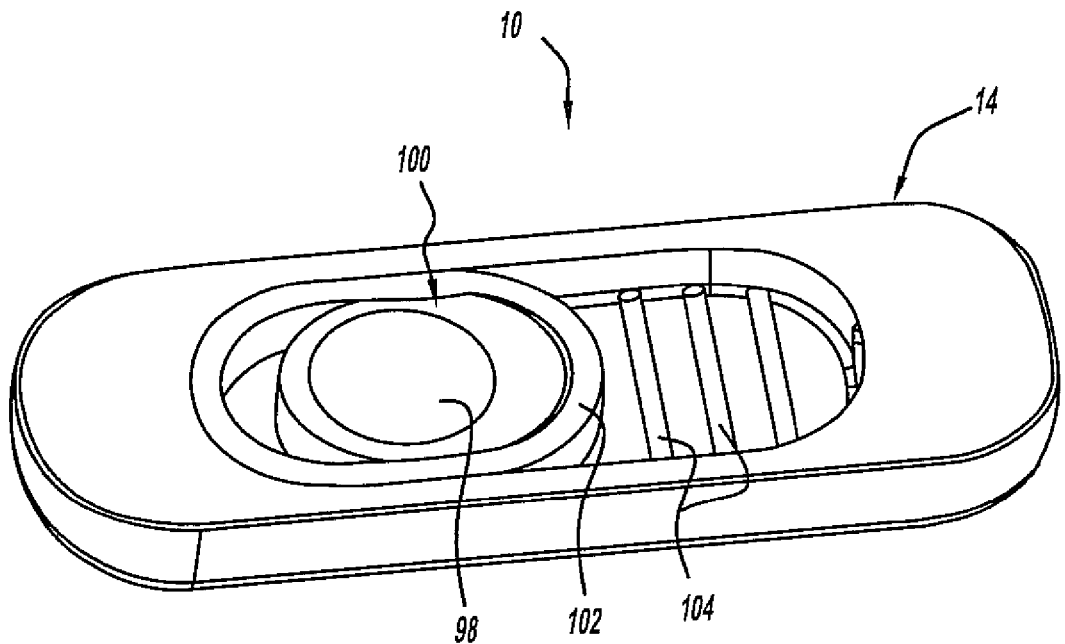
FIG. 33 shows a further embodiment of the present invention.

FIG. 32 shows the bearing member 16 such that the bottom of the base portion 50 (not shown) is abutting the ramp portion 92 (not shown). The bearing seating cavity 94 is shallower than the deepest portion of the ramp portion 92, as described in earlier embodiments, such that when the bearing member 16 is moved into the cavity 94, the bearing member 16 maintains a greater height above the outer wall 96 of the upper housing member 12. This creates a gap between the housings 12, 14 to allow relative motion therebetween. FIG. 33 shows an additional embodiment, wherein the lower housing 14 includes a bearing member receiving member 100 including a concave surface 98 for accepting the inverted bearing member 16, the bearing member 16 including its base portion 50 exposed within the cavity of the upper bearing member 12, as discussed above and shown in FIGS. 31 and 32. Member 100 is configured to be oblong so as to prevent rotation thereof. It is contained within an oblong ring member 102, which locks along recesses 104 as described above. Member 100 is allowed to move within ring member 102, thereby allowing for natural realignment, as discussed above. Also, the center of rotation can be adjusted by the surgeon by moving the ring member 102 relative to the cavity containing the recesses 104, as discussed above.

Figure 34:
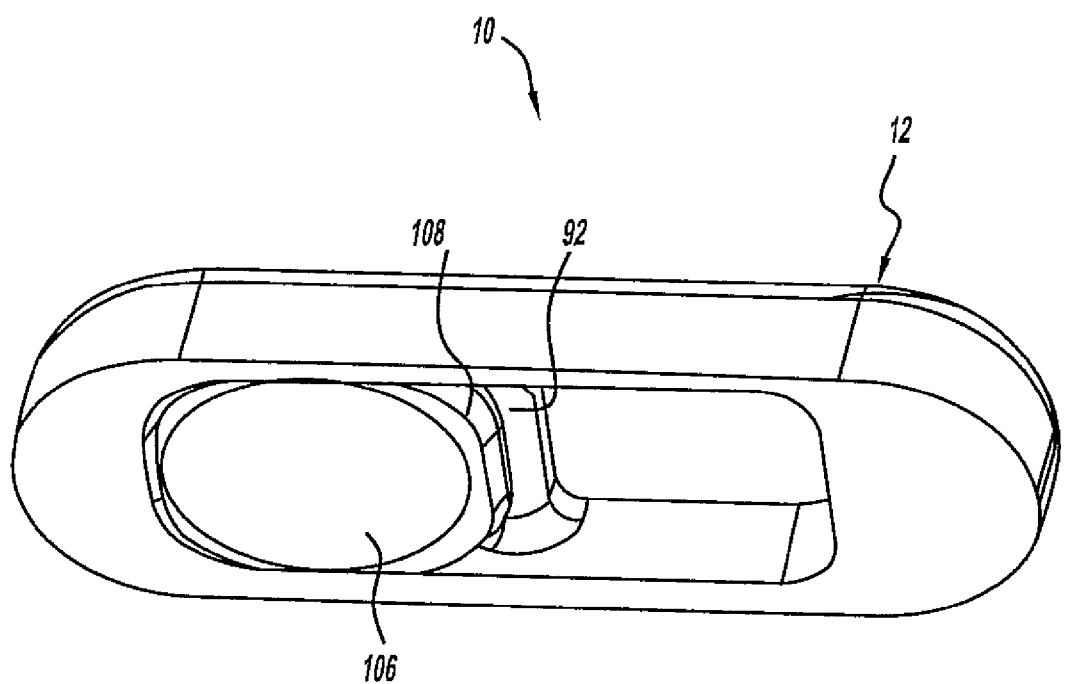
FIG. 34 shows a further embodiment of the present invention made in accordance with the present invention.

FIG. 34 shows an upper housing 12 including a concave cavity 106 disposed within a member 108 capable of sliding along the ramp portion 92. In this manner, the upper housing member 12 includes a concave cavity adjustable relative to the housing member 12.

Figure 35:
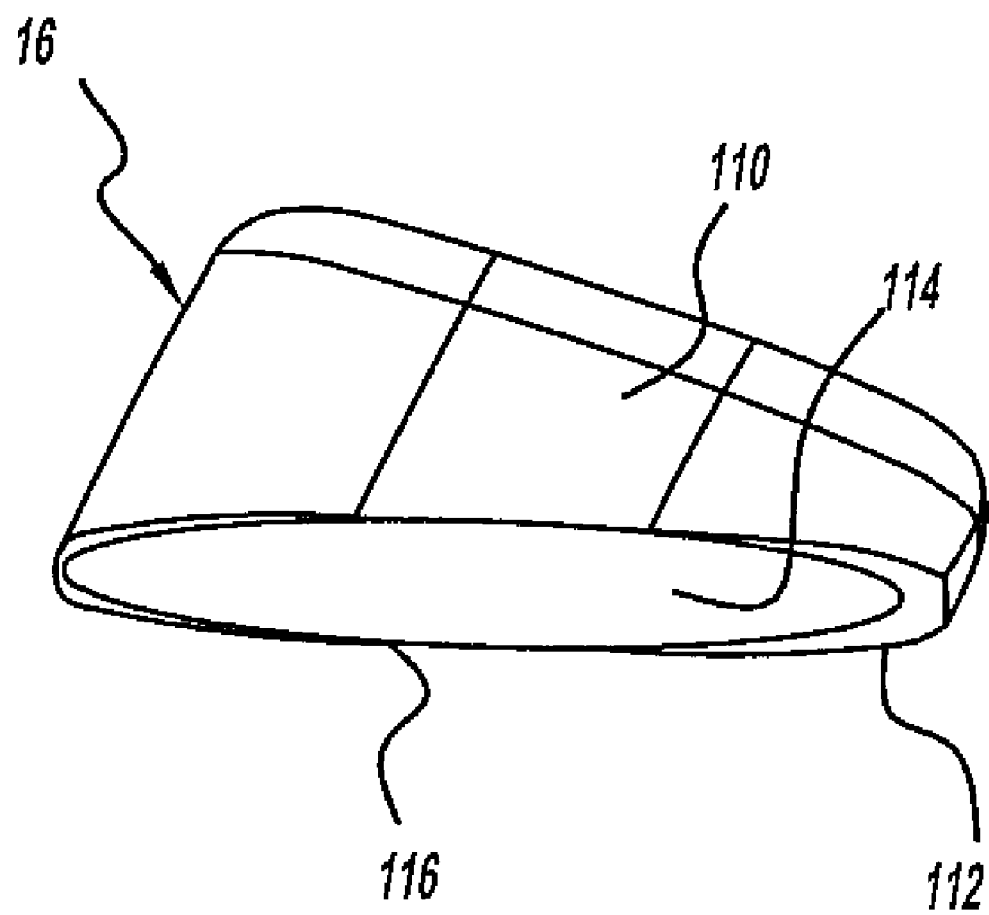
FIG. 35 shows a further embodiment of the bearing member constructed in accordance with the present invention.

FIG. 35 shows a bearing member 110 including a base portion 112, including the concave cavity 114. The bearing member 16 includes a bearing portion 116 cut at an angle, thereby allowing the bearing member 16 to be contained within the upper housing ramp area, which is angled relative to the floor portion of the lower housing member 14 and presents a relatively parallel surface to the floor portion because of the angled surface 116.

In view of the above multiple embodiments, the present invention provides several unique aspects to a spinal implant assembly. The spinal implant assembly 10 includes a self-contained distracting mechanism for distracting the housing halves 12, 14 from a first condition in which the housing halves 12, 14 are floatable into the intervertebral space to a second condition in which the housing halves 12, 14 are distracted to fixedly engage and distract the opposing vertebral surfaces defining the intervertebral space. The distracting mechanism is contained within the housing halves 12, 14, thereby obviating the need for a distracting instrument. The present invention further provides an adjustment mechanism for adjusting a center of rotation of the assembly relative to the intervertebral space after the assembly 10 has been inserted into the intervertebral space. Further, the present invention provides a novel insert member for a spinal implant assembly, the insert member 16 including a cylindrical portion including a first end having a substantially flat surface and a hemispherical bearing portion operably connected to the second end of the cylindrical portion.

The present invention further provides several novel aspects with regards to methods of inserting a spinal implant assembly into an intervertebral space, as discussed above in more detail. The inventive method includes a novel step of inserting the spinal implant assembly into an intervertebral space and then distracting the spinal implant assembly from a first condition in which the spinal implant assembly is floatable into the intervertebral space to a second condition in which the assembly is distracted to fixedly engage opposing vertebral surfaces, defining the intervertebral space, wherein the spinal implant assembly is the distracting mechanism. The spinal implant assembly can be retracted after implantation into the intervertebral space to either adjust the distraction height and/or remove the implant assembly from the intervertebral space all back in the first condition. Thus, the spinal implant assembly can be distracted into the second condition while expanding the intervertebral space, depending on the extent to which the bearing member 16 expands the height of the two housing halves 12, 14.

The present invention further provides a unique step of adjusting a center of rotation of a spinal implant assembly 10 after the assembly has been inserted into the intervertebral space. This is accomplished by assembly 10 as exemplified in various of the embodiments, the invention allowing for either free movement of the bearing member to provide self adjustment and/or re-fixing of the bearing member relative to the two housing halves by being either directly engageable with a floor 30 of a housing member or by being seated within a cage member, which itself is engageable with the floor portion 30 of the housing member.

Most generally, the present invention provides a method of inserting a spinal implant assembly into an intervertebral space, by including the steps of inserting the spinal implant assembly 10 into the intervertebral space, stabilizing the intervertebral space by expansion of the height of the housing halves 12, 14 and restoring anatomical motion to the vertebrae defined in the intervertebral space. This restoration is achieved through the various embodiments of the housing members 12, 14 and bearing member 16. In view of the total of the above, the present invention is uniquely capable of being posteriorly inserted as a pair of spinal implant assemblies into an intervertebral space since the center of rotation can be adjusted independently in each of the implants in situ.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

REFERENCES

U.S. Patents
U.S. Pat. No. 6,443,987 B1
U.S. Pat. No. 6,001,130
U.S. Pat. No. 5,258,031
U.S. Pat. No. 5,314,477
U.S. Publications
2004/0225363

What is claimed is:

1. A spinal implant assembly comprising
   housing means for containing a bearing member completely therein and seating within an intervertebral space;
   bearing means disposed within said housing for enabling disc like movement between vertebrae defining the intervertebral space; and
   distracting means disposed within said housing for distracting said housing means from a first condition in which said housing means is floatable into the intervertebral space to a second condition in which said housing means is distracted to fixedly engage the opposing vertebral surfaces defining the intervertebral space, said housing means including at least a first and second housing member for containing said bearing means therein and therebetween, at least one of said housing means including a ramping surface over which said bearing means seats and travels defining said distracting means whereby translating of said bearing means from a first position on said ramping surface to a second position on said ramping surface distracts said housing means from said first condition to said second condition without displacing said housing members relative to each other;
   wherein said bearing means includes a bearing head including a bearing surface thereon and a bottom portion seated against a ramping surface within an internal housing cavity; and
   wherein said bearing head includes connecting means for connecting said bearing head to said bottom portion.

2. The spinal implant assembly as set forth in claim 1, wherein each of said housing members includes a recessed opening therein juxtaposed to each other defining an internal housing cavity, and seating said bearing means therein, at least one of said recessed openings including said ramping surface.

3. The spinal implant assembly as set forth in claim 2, wherein said ramping surface includes a bearing seating cavity recessed relative to a high point of said ramping surface, said high point producing maximal distraction of said housing when said bearing means is seated thereon, said bearing means being restricted from further translation on said ramping surface when said bearing means is seated in said bearing seating cavity.

4. The spinal implant assembly as set forth in claim 3, wherein said bearing seating cavity seats said bearing means at a desired center of rotation.

5. The spinal implant assembly as set forth in claim 4, including center of motion adjustment means for adjusting the position of said bearing means relative to said housing while said bearing means is seated in said bearing seating cavity and after said assembly is distracted within a vertebral space.

6. The spinal implant assembly as set forth in claim 5, wherein said center of motion adjustment means includes a base member seated within said internal housing cavity for translation over said ramping surface, said bearing means being seated therein, said assembly including ratcheting engagement means for defining engagement sites between said base member and said ramping surface and locking said base member in any of several positions relative to said internal housing cavity, thereby allowing the center of rotation of said assembly to be adjusted.

7. The spinal implant assembly as set forth in claim 6, wherein one of said base member and ramping surface include projections and the other includes recesses for engaging each other and defining said engagement means.

8. The spinal implant assembly as set forth in claim 7, wherein said bearing means includes a cylindrical portion seated within said bearing seating cavity and against said ramping surface and a hemispherical portion integrally connected thereto providing a bearing surface against a bearing surface of said internal housing cavity, opposite said ramping surface.

9. The spinal implant assembly as set forth in claim 8, wherein said hemispherical portion includes a highly polished hemispherical surface.

10. The spinal implant assembly as set forth in claim 9, wherein said hemispherical surface includes a treatment selected from the group including diamond-like coatings and titanium nitrate.

11. The spinal implant assembly as set forth in claim 10, wherein said bearing means includes anti-rotation means for preventing rotation of said bearing means relative to said internal housing cavity.

12. The spinal implant assembly as set forth in claim 11, wherein said bearing means includes an oblong portion defining said anti-rotation means seated against said ramping surface and a hemispherical portion integrally connected thereto providing a bearing surface against a bearing surface of said internal housing cavity opposite said ramping surface.

13. The spinal implant assembly as set forth in claim 12, wherein said hemispherical portion includes a highly polished hemispherical surface.

14. The spinal implant assembly as set forth in claim 13, wherein said hemispherical surface includes a treatment selected from the group including diamond-like coatings and titanium nitrate.

15. The spinal implant assembly as set forth in claim 8, wherein said internal housing cavity is larger than a largest cross-sectional dimension of said cylindrical portion providing clearance therebetween and allowing said bearing means to free float along a length of said internal housing cavity thereby allowing adjustments of a center of rotation between more than one of said assemblies.

16. The spinal implant assembly as set forth in claim 2, including a base member disposed within said internal housing cavity for containing said bearing means therein and biasing means disposed between said base member and said ramping surface provided cushioned movement of said base member towards and away from said ramping surface thereby allowing lateral bending of vertebrae about said spinal implant assembly.

17. The spinal implant assembly as set forth in claim 1, wherein said bearing head and said bottom portion are an integral unit.

18. The spinal implant assembly as set forth in claim 1, including biasing means interconnecting said bearing head and said bottom portion allowing relative controlled motion therebetween.

19. The spinal implant assembly as set forth in claim 18, wherein said bearing head includes an internal pocket having an annular recess therein and said bottom portion including an annular recess therein and said biasing means including an annular spring member fixedly seated in and sandwiched between said recesses.

\* \* \* \* \*